(12) United States Patent
Mertz et al.

(10) Patent No.: US 11,022,591 B2
(45) Date of Patent: Jun. 1, 2021

(54) SYSTEM AND METHOD FOR REAL TIME MEASUREMENT OF CHLORINE CONTAINING COMPOUNDS IN COMBUSTION OR PROCESS GAS

(71) Applicant: Ohio Lumex Co., Inc., Cleveland, OH (US)

(72) Inventors: Andrew Mertz, Mantua, OH (US); Joseph Siperstein, Chagrin Falls, OH (US)

(73) Assignee: Ohio Lumex Co., Inc., Cleveland, OH (US)

( * ) Notice: Subject to any disclaimer, the term of this patent is extended or adjusted under 35 U.S.C. 154(b) by 244 days.

(21) Appl. No.: 16/447,317

(22) Filed: Jun. 20, 2019

(65) Prior Publication Data

US 2019/0391123 A1    Dec. 26, 2019

Related U.S. Application Data

(60) Provisional application No. 62/689,452, filed on Jun. 25, 2018.

(51) Int. Cl.
*G01N 33/00* (2006.01)
*B01D 53/02* (2006.01)

(52) U.S. Cl.
CPC ..... *G01N 33/0047* (2013.01); *G01N 33/0073* (2013.01); *B01D 53/02* (2013.01)

(58) Field of Classification Search
CPC . G01N 33/0047; G01N 33/0073; B01D 53/02
USPC ........................................................ 73/23.31
See application file for complete search history.

(56) References Cited

U.S. PATENT DOCUMENTS

| | | | |
|---|---|---|---|
| 9,181,499 B2 | 11/2015 | Mason et al. | |
| 2011/0184211 A1 | 7/2011 | Van Driessche et al. | |
| 2014/0198898 A1 | 7/2014 | Beumer et al. | |
| 2014/0296607 A1* | 10/2014 | Baptist | B01D 15/1871 585/822 |

OTHER PUBLICATIONS

Johnson Matthey, Puraspec Clear Chloride guards brochure, 2015, pp. 1-16.

(Continued)

*Primary Examiner* — Tarun Sinha
(74) *Attorney, Agent, or Firm* — Renner, Otto, Boisselle & Sklar, LLP (57) ABSTRACT

The present disclosure provides a system and method for real time speciated or total measurement of chlorine containing compounds, specifically HCl and RCl, in combustion or process gas generated at refineries. The system may include a sample inlet line, a zero-filter, an RCl converter, an HCl analyzer, and an exhaust line. At least one valve may divert a sample gas to the components of the system. Plain lines and connectors connect the components of the system. The system may be installed as part of a continuous assembly or separate from an industrial operation unit in a facility. The method of measuring the chlorine concentration in the sample gas includes operating the system in a plurality of separate modes such that the sample gas is diverted to the different components of the system and analyzed accordingly.

19 Claims, 2 Drawing Sheets

(56) References Cited

OTHER PUBLICATIONS

Johnson Matthey, Puraspec Chloride Removal Absorbents, retrieved online in May 2018 from: http://www.improtech.com/chloride-removal-absorbents-johnson-matthey.

Testo, Flue Gas Analysis in Industry, Practical Guide for Emission and Process Measurements, 2004, pp. 1-149.

Mani Erfan, Chloride removal in refineries, Catalysis, 2011, pp. 1-10, available at www.digitalrefining.com/article/1000407.

XOS, Discover How to Manage Chloride in the Refinery Crude Unit eBook, pp. 1-29, retrieved online in May 2018 from: https://www.xos.com/cms-portals/xos_com/cms/documents/pdf/Case-Studies/Discover-How-to-Manage-Chloride-in-the-Refinery-Crude-Unit-eBook.pdf.

* cited by examiner

SYSTEM AND METHOD FOR REAL TIME MEASUREMENT OF CHLORINE CONTAINING COMPOUNDS IN COMBUSTION OR PROCESS GAS

RELATED APPLICATIONS

This application claims the benefit of U.S. Provisional Application No. 62/689,452 filed Jun. 25, 2018, which is hereby incorporated herein by reference.

TECHNICAL FIELD

The present disclosure relates to industrial process monitoring of contaminants, such as for internal quality control purposes and for externally mandated requirements, and more particularly to a system and method for real time speciated or total measurement of chlorine containing compounds, specifically HCl and RCI, in combustion or process gas, such as that which is generated at a refinery.

BACKGROUND

Industrial facilities, such as refineries, must remove hydrogen chloride ("HCP") and organic chlorides ("RCI") from their combustion or process gas before exhausting the gaseous waste into the atmosphere to comply with regulations or to prevent corrosion and fouling of valuable equipment. Typically, this removal is accomplished with wet or dry scrubbing units although several other types of scrubbing units are in the operating fleet. To optimize the scrubbers and to monitor their efficiency, the concentrations of gas-phase HCl and RCI should be adequately measured.

Currently, a color-based indicator is used to detect variances in HCl and RCI levels. This conventional methodology outputs results in real time but with poor precision and accuracy. Alternatively, samples of the gas stream can be collected and sent off-site for more accurate analysis. There are few laboratories able to perform a speciated HCl and RCI analysis in a gaseous matrix and the samples will not be analyzed quickly enough to provide technicians with the information they need to make timely adjustments.

SUMMARY

The present disclosure provides a system and method for real time speciated or total measurement of chlorine containing compounds, specifically HCl and RCI, in combustion or process gas, such as that generated at refineries.

The system may include a sample inlet line, a zero-filter, an RCI converter, an HCl analyzer, and/or an exhaust line. At least one valve may divert a sample gas to the components of the system. Plain lines and connectors may connect the components of the system. The system may be installed as part of a continuous assembly or separate from an industrial operation unit in a facility. The method of measuring the chlorine concentration in the sample gas includes operating the system in a plurality of modes such that the sample gas is diverted to the different components of the system and analyzed accordingly.

According to an aspect of the present disclosure, a measurement system for real-time measurement of RCI content in a sample gas taken from a combustion or process gas stream, includes: a sample inlet for receiving the sample gas from the combustion or process gas stream; an RCI converter downstream of the sample inlet for receiving the sample gas, the RCI converter being configured to convert RCI contained in the sample gas to HCl; and an HCl analyzer downstream of the RCI converter, the RCI converter being configured to measure an amount of HCl contained in the sample gas; wherein the system is configured to operate in at least a first state, in which the sample gas flows through the RCI converter and the RCI contained in the sample gas is converted to HCl thereby forming a converted sample gas, said converted sample gas flowing downstream to the HCl analyzer when the system is in the first state for measuring the amount of HCl contained therein; wherein the system is configured to operate in at least a second state, in which at least some of the sample gas bypasses the RCI converter and avoids conversion of the RCI to HCl as unconverted sample gas, said unconverted sample gas flowing into the HCl analyzer for measuring the amount of HCl contained therein; and wherein the RCI content in the sample gas is determinable based upon a difference in at least: (i) the amount of HCl contained in the converted sample gas as measured by the HCl analyzer when the system is in the first state, and (ii) the amount of HCl contained in the unconverted sample gas as measured by the HCl analyzer when the system is in the second state.

According to another aspect of the present disclosure, a system for real-time measurement of total chloride content of HCl and RCI in a combustion or process gas, includes: an inlet for receiving the combustion or process gas; an RCI converter downstream of the inlet and configured to convert RCI contained in the combustion gas to HCl; and an HCl analyzer downstream of the RCI converter, the HCL analyzer being configured to measure an amount of HCl in the combustion or process gas; wherein the HCl analyzer is configured to determine the total chloride content of HCl and RCI in the combustion or process gas based upon the measured amount of HCl in the process gas received from the RCI converter, and is configured to output the results.

According to another aspect of the present disclosure, a method of real-time measurement of RCI content in a sample gas taken from a combustion or process gas stream, includes: (i) conveying the sample gas from the combustion or process gas stream into an inlet of a measurement system; (ii) operating the measurement system in a first mode, including: conveying the sample gas from the inlet to an RCI converter; converting the RCI contained in the sample gas to HCl with the RCI converter, thereby forming a converted sample gas; conveying the converted sample gas to an HCl analyzer; measuring an amount of HCl in the converted sample gas with the HCl analyzer; (iii) operating the measurement system in a second mode, including: conveying the sample gas from the inlet; bypassing the RCI converter such that the sample gas is unconverted sample gas; conveying the unconverted sample gas to the HCl analyzer; measuring an amount of HCl in the unconverted sample gas with the HCl analyzer; and (iv) determining an amount of RCI in the sample gas by calculating a difference between the measurement from the first mode and the measurement from the second mode.

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

All numerical ranges disclosed in the specification and claims may be combined in any manner. It is to be understood that unless specifically stated otherwise, references to "a," "an," and/or "the" may include one or more than one, and that reference to an item in the singular may also include the item in the plural. All combinations specified in the claims may be combined in any manner.

The present disclosure provides a system and method for real time speciated or measurement of chlorine containing compounds, specifically HCl (hydrogen chloride, or hydrochloric acid) and RCl, in combustion or process gas. As used herein, "RCl" means organic chlorides, and includes, for example, chloroform ($CH_3$—Cl), carbon tetrachloride (C—$Cl_4$), tetrachlorethylene ($Cl_2$—C=C—$Cl_2$), vinyl chloride ($C_2H_3Cl$), chlorobenzene ($C_6H_5Cl$), Freon ($C_2Cl_3$), chloroprene ($CH_2$=CClCH=$CH_2$), propylene dichloride ($C_3H_6Cl_2$), dichloromethane ($CH_2CL_2$) and trichloroethylene (CHCl=$CCl_2$).

In contrast with conventional color-based tests or off-site analysis, the system of the present disclosure provides accurate, real time speciated or total measurements of HCl and RCl concentrations on-site. An exemplary system includes a sample inlet line, an RCl converter, an HCl analyzer, and an exhaust line. The system also may further include a zero-filter, chemically inert tubing joining the components, and at least one valve directing the flow of the sample gas to the components. A method of measuring the chlorine concentration in the sample gas includes operating the system in a plurality of separate modes such that the sample gas is diverted to the different components of the system and analyzed accordingly.

Figure 1:
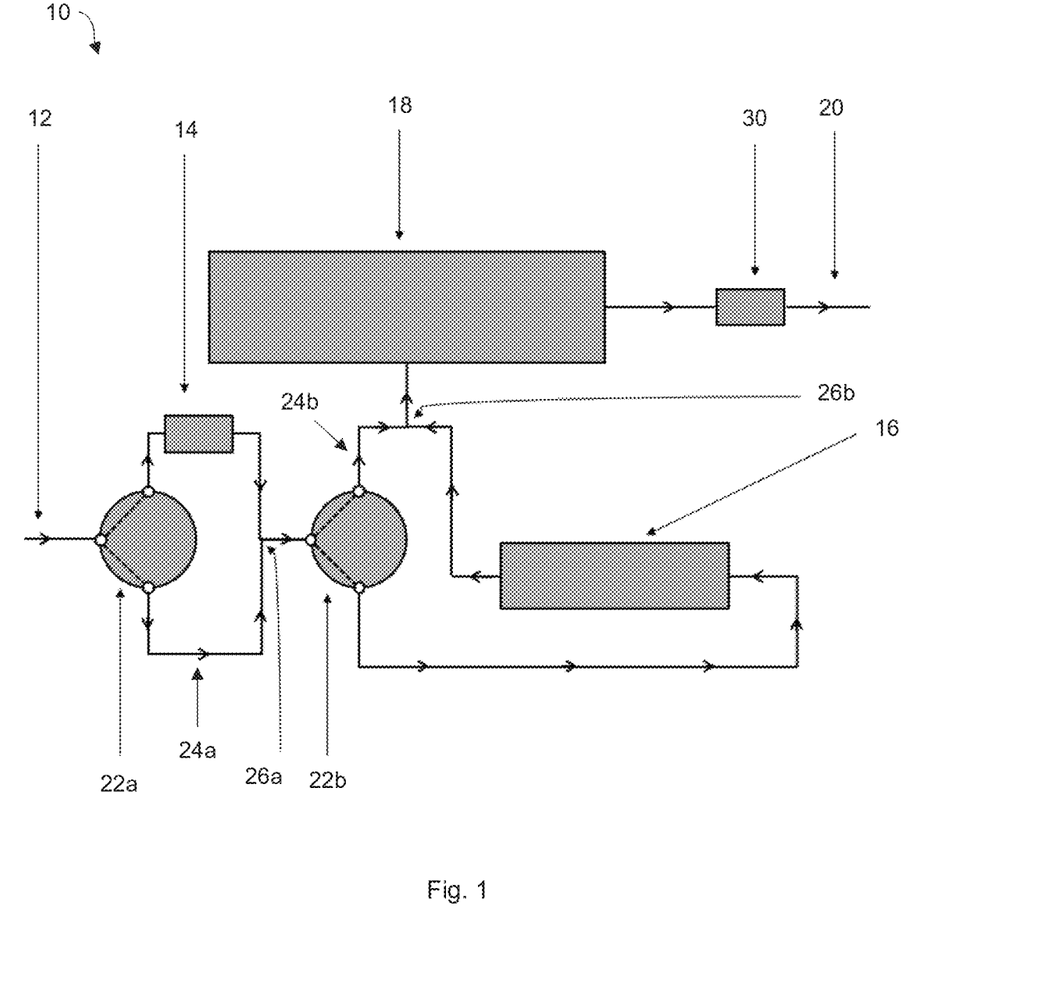
FIG. 1 is a schematic view of an exemplary system according to the present disclosure for real time speciated measurement of chlorine containing compounds in combustion or process gas.

Referring now in detail to FIG. 1, an exemplary system for real time speciated measurement of chlorine containing compounds is shown at 10. The system 10 includes a sample inlet line 12, a zero-filter 14, an RCl converter 16, an HCl analyzer 18, and an exhaust line 20. One or more valves, including a first valve 22a and a second valve 22b, are configured to direct a sample gas to the components of the system 10. The valves 22a and 22b may be any suitable type of valve for directing the sample gas through the system 10. In the illustrated embodiment, for example, the valves 22a and 22b are configured as diverter valves, such as three-way valves. As shown, the two sets of dashed lines in each of the valves 22a and 22b of FIG. 1 indicate that either path in each valve may be open to the flow of the sample gas, but in exemplary embodiment both paths in each valve are not opened simultaneously. The system 10 also includes a plurality of plain lines, such as first plain line 24a and second plain line 24b, and connectors 26a and 26b to connect the components of the system 10.

As shown, the system 10 includes a gas circuit for conveying the sample gas to the different components of the system 10. For example, the gas circuit includes fluid conduits, such as suitable gas tubing. The tubing of the system 10, including the sample inlet line 12, plain lines 24a, 24b, connectors 26a, 26b, and exhaust line 20, may be made of a chemically inert material, such as polytetrafluoroethylene (e.g., Teflon™), silicone, vinyl, fluroelastomer, fluorinated ethylene propylene, polyethylene, or a combination thereof.

The zero-filter 14 may be any suitable filter that filters HCl and RCl out of the sample gas such that a baseline may be established. The zero-filter 14 may be a granular bed filter having a chamber packed with a solid, granular base such as gravel, sand, pelletized fly ash, or other suitable material. The zero-filter 14 may be an impinger containing materials, such as an alkali solution, that will collect the chlorine containing compounds in the sample gas.

The RCl converter 16 is any suitable device that converts RCl to HCl via thermal decomposition or other catalytic or chemical process. In preferred embodiments, the RCl converter 16 utilizes thermal decomposition to convert the RCl contained in the sample gas to HCl. The RCl converter 16 may have an inlet for ingress of the sample gas, a heated chamber for thermal decomposition and conversion of the RCl to HCl in the sample gas, and one or more outlets for egress of the sample gas. For example, in some embodiments, one outlet may be utilized for conveying the converted sample gas (i.e., the sample gas having HCl converted from RCl) out of the RCl converter 16, while a waste component of the sample gas (e.g., the gas containing the organic component(s) of the RCl molecules after the HCl conversion) may exit the chamber via a separate outlet. The waste gas may be sent back to the combustion or process gas stream, may be vented to atmosphere, and/or may be sent through a scrubber. Alternatively, the RCl converter 16 may have one outlet for egress of both the converted sample gas and the waste component which may pass through a scrubber for capturing the waste component. The converted sample gas may pass through the scrubber for analysis by the HCl analyzer 18, as discussed in further detail below.

The efficiency of the conversion of RCl to HCl in the sample gas may be dependent on the temperature utilized by the RCl converter 16. The temperature of the RCl converter 16 may be in the range of about 50° C. to 1000° C., or in another example, in the range of 200° C. to 800° C., or in another example, in the range of 400° C. to 600° C., or in another example in the range of 50° C. to 300° C., more particularly in the range of 50° C. to 150° C. In a preferred embodiment, the RCl converter 16 has a temperature of 50° C. to 500° C. to ensure complete decomposition, although the temperature of the decomposition may vary based on the organic components of the RCl molecules. Alternatively or additionally, the RCl converter 16 may include a catalyst or other reagent. The catalyst contained in the RCl converter 16 may include palladium, platinum, rhodium, nickel, cobalt, ruthenium, iridium, copper, rhenium, or a combination thereof.

The HCl analyzer 18 is any suitable device that measures the amount (e.g., concentration) of HCl in the sample gas. The HCl analyzer outputs this measurement information, which may be used by a processor or other controller to take further action and/or may be outputted for interpretation by an operator. The HCl analyzer 18 may be any of several commercially available analyzers that measure gas phase HCl, including Tunable Diode Laser Absorption Spectroscopy (TDL), Fourier Transform Infra-Red Spectroscopy (FTIR), Non-Dispersive Infrared (NDIR), or Chemical Ionization Time-of-flight Mass Spectrometry (CI-ToFMS). In preferred embodiments, the HCl analyzer is TDL.

The HCl analyzer 18 may be capable of measuring HCl content of about 3,000 ppm or less. In further embodiments, the HCl analyzer 18 is capable of measuring HCl content of about 3,000 ppm or less, about 2,000 ppm or less, about 1,000 ppm or less, about 900 ppm or less, about 800 ppm or less, about 700 ppm or less, about 600 ppm or less, about 500 ppm, or less, about 400 ppm or less, about 300 ppm or less, about 200 ppm or less, about 100 ppm or less, about 90 ppm or less, about 80 ppm or less, about 70 ppm or less, about 60 ppm or less, about 50 ppm or less, about 40 ppm or less, about 30 ppm or less, about 20 ppm or less, about 10 ppm or less, about 9 ppm or less, about 8 ppm or less, about 7 ppm or less, about 6 ppm or less, about 5 ppm or less, about 4 ppm or less, about 3 ppm or less, about 2 ppm or less, or about 1 ppm or less. The HCl analyzer 18 may provide real time automated measurements of the HCl concentration, such as via a processor or other controller.

An exemplary operation of the preferred embodiment of the system 10 will now be described below. This preferred embodiment is non-limiting and it should be appreciated that there are several comparable arrangements of the system 10. These various arrangements are acceptable provided that the system and/or operator reasonably modulate the flow of gas through the zero-filter 14, the RCI converter 16, and/or the HCl analyzer 18.

As shown, the sample gas enters the system 10 from a combustion or process gas stream through sample inlet line 12. The system 10 may be installed as part of a continuous assembly or separate from an industrial operation unit in a facility such as a refinery. As such, the sample gas may enter the system 10 directly from a constant gas stream in an industrial assembly, or the sample gas from the combustion or process gas stream may enter the system 10 from another source such as a cylinder. The sample gas may be introduced into the sample inlet line 12 using any suitable means such as a pump, a valve, an injector, piping, or other instrumentation. The flow of the sample gas (as indicated by open arrow-heads in FIG. 1) through the system 10 should be sufficient to keep the sample gas flowing towards the HCl analyzer 18. The system 10 may include a pump 30 to induce a known flow through the system 10 at a constant or variable rate. The pump 30 may be used if the flow from the gas stream's back pressure is insufficient or inconsistent. In the illustrated embodiment, the pump 30 is downstream of the HCL analyzer 18 and upstream of the exhaust 20, however it is understood that the pump 30 may be located at any suitable location in the system 10 or connected to the gas circuit of the system 10. The system 10 is preferably free from leaks. If the sample gas is volatile or flammable in nature, the system 10 is preferably contained in an explosion proof or purged enclosure.

The sample gas flows through the sample inlet line 12 into first valve 22a. As illustrated, the first valve 22a is a three-way valve that outlets either to the zero-filter 14 or to the first plain line 24a. If the first valve 22a is in a first state and open to the zero-filter 14, all of the chlorides, such as from both the HCl and RCI, are removed from the sample gas stream. If the first valve 22a is in a second state and open to the first plain line 24a, then the sample gas bypasses the zero-filter 14 and is not altered as the sample gas flows through the first plain line 24a to the next component (e.g., valve 22b or RCI converter 16).

After the sample gas flows through either the zero-filter 14 or the first plain line 24a, the sample gas flow is directed to the second valve 22b via the connector 26a (e.g., splitter or T-connector). As illustrated, the second valve 22b is a three-way valve that outlets either to the RCI converter 16 or the second plain line 24b. If the second valve 22b is in a first state and open to the RCI converter 16, any RCI passing through the RCI converter 16 is transformed into HCl thereby forming the converted sample gas which is then be passed to the HCl analyzer 18. If the second valve 22b is in a second state and open to the second plain line 24b, then the sample gas bypasses the RCI converter 16 and is not altered as this unconverted sample gas flows through the plain line 24b to the next component (e.g., HCl analyzer 18).

After the sample gas flows through either the RCI converter 16 or the second plain line 24b, the sample gas (converted or unconverted) is directed to the HCl analyzer 18 via the connector 26b for measuring the amount of HCl contained therein.

In exemplary embodiments, the system 10 includes a system controller that is operably coupled to at least the first valve 22a, the second valve 22b, the RCI converter 16, the HCl analyzer 18, and/or the pump 30 to control the operation thereof. The system controller may receive information from one or more sensors in the system 10 and/or the various components therein to control one or more parameters, such as temperature, flow rate, etc. For example, the system controller may be operably connected to the pump 30 and configured to control a flow rate of the sample gas through the system 10. The system controller may be operably connected to the RCI converter 16 and configured to control one or more parameters associated with the conversion of the RCI contained in the sample gas to HCl, such as controlling the temperature of the heated chamber in the RCI converter 16. As discussed above, the HCl analyzer 18 is configured to perform real time automated measurements of the HCl concentration in the sample gas (converted or unconverted), such as via a processor or other controller, and output this information for determination, as discussed in further detail below. The system controller may cooperate with the HCl analyzer 18 for receiving the information from the HCl analyzer 18, or the controller of the HCl analyzer 18 may be formed as part of the system controller. The system controller may be operably connected to the first and/or second valves 22a, 22b and configured to switch the valve(s) 22a, 22b between the first and second states in one or more operational modes, as discussed below.

In a first system mode corresponding to a first state of the system 10, the first valve 22a is in its first state and directs the sample gas to the zero-filter 14. Also in the first mode, the second valve 22b is in its second state and directs the filtered sample gas to the HCl analyzer 18 via the second plain line 24b. In the first mode, the HCl analyzer 18 reads or should be adjusted to read zero (i.e., no chlorine compounds detected).

In a second system mode corresponding to a second state of the system 10, the first valve 22a is in its second state and bypasses the zero-filter 14, such that the sample gas is directed to the first plain line 24a. In the second mode, the second valve 22b is in its second state and bypasses the RCI converter 16, such that this unconverted sample gas is directed to the HCl analyzer 18 via the second plain line 24b. In the second mode, the HCl analyzer 18 detects and measures only the native HCl in the unconverted sample gas, and not the RCI contained therein.

In a third system mode corresponding to a third state of the system 10, the first valve 22a is in its second state and directs the sample gas to the first plain line 24a. In the second mode, the second valve 22b is in its first state and directs the sample gas to the RCI converter 26, which converts the RCI in the sample gas to HCl. This converted sample gas is then passed to the HCl analyzer 18, which detects and measures the total chloride amount of the converted sample gas (i.e., both the native HCl already present in the sample gas in addition to the HCl in the sample gas caused by the conversion of RCl to HCl).

By subtracting the only native HCl measurement (i.e., the unconverted sample gas from the second mode) from the total chloride measurement (i.e., the converted sample gas from the third mode), the RCl concentration of the sample gas may be determined based upon the difference. In this manner, the exemplary system 10 provides real-time speciated measurement of chlorine containing compounds in the sample gas. In exemplary embodiments, the HCl analyzer 18 is configured to perform this determination of the RCl concentration, or the determination may be performed manually by an operator. It is understood that the system 10 may be operated in any of the first, second, or third system modes.

After the sample gas flows through the HCl analyzer 18, the sample gas may exit the system 10 through the exhaust line 20. The sample gas may be exhausted wherever the operator or system designer deems it appropriate to do so.

The system 10 may include an HCl scrubbing unit after the HCl analyzer 18 or after the exhaust line 20 to prevent damage to equipment. The HCl scrubbing unit may include a hydrogen halide sorbent that captures the HCl. The sorbent may include, for example, carbon, alumina, alkalized metal oxides such as alkalized alumina, alkalized silica, and alkalized aluminosilicate, or a combination thereof. The sorbent may include a zinc component selected from a zinc oxide, hydroxide, carbonate, bicarbonate, basic carbonate, or a combination thereof. The sorbent may include a basic metal component selected from at least one compound of at least one alkali or alkaline earth metal. The sorbent may contain a binder made of a suitable hydraulic cement, for example calcium aluminate cement, or a clay, for example an acicular clay such as attapulgite or spiolite clay. The sorbent may be made by pelleting, granulating, or extruding a mixture of alumina or a hydrated alumina such as alumina trihydrate, a basic metal component, optionally the zing component, and the binder in the requisite proportions and calcining the resultant mixture.

Figure 2:
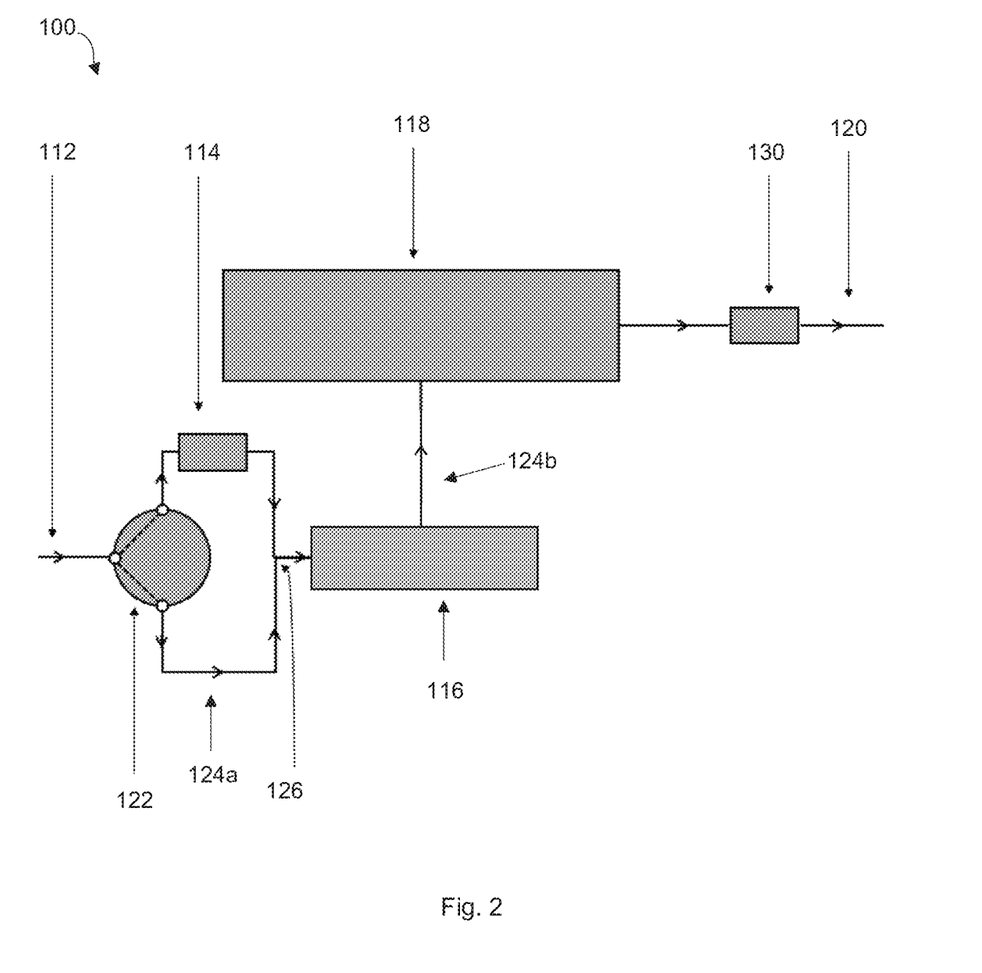
FIG. 2 is a schematic view of an exemplary system according to the present disclosure for total measurement of chlorine containing compounds in combustion or process gas.

Referring now to FIG. 2, an exemplary system for total measurement of chlorine containing compounds is shown at 100. The features of the components of the system 100 are similar to the features of the components of system 10 (FIG. 1), and consequently the same reference numerals but indexed by 100 are used to denote structures corresponding to the same or similar structures in the systems 10, 100. In addition, the foregoing description of the system 10 is equally applicable to the system 100, except as noted below. It is also understood that aspects of the systems 10, 100 may be substituted for one another or used in conjunction with one another where applicable.

As shown, the system 100 includes a sample inlet line 112, a zero-filter 114, an RCl converter 116, an HCl analyzer 118, and an exhaust line 120. A valve 122 diverts a sample gas to either the zero-filter 114 or a first plain line 124a. The two sets of lines in the valve 122 of FIG. 1 indicate that either path in the valve may be open to the flow of gas, but in exemplary embodiments both paths in each valve are not simultaneously opened. The system 100 also includes a connector 126 and a second plain line 124b.

A preferred embodiment of the configuration of the system 100 is shown in FIG. 2 and will be described below. This preferred embodiment is non-limiting and it should be appreciated that there are several comparable arrangements of the system 100. These various arrangements are acceptable provided that the system and/or operator may reasonably modulate the flow of gas through the zero-filter 114, the RCl converter 116, and the HCl analyzer 118.

The sample gas enters the system 100 through sample inlet line 112. The system 100 may be installed as part of a continuous assembly or separate from an industrial operation unit in a facility such as a refinery. As such, the sample gas may enter the system 100 directly from a constant gas stream in an industrial assembly or the sample gas may enter the system 100 from another source such as a cylinder. The sample gas may be introduced into the sample inlet line 112 using any suitable means such as a pump, a valve, an injector, piping, or other instrumentation. The flow of the sample gas (as indicated by open arrow-heads in FIG. 2) through the system 100 should be sufficient to keep the sample gas flowing towards the HCl analyzer 118. The system 100 may include a pump 130 to induce a known flow through the system 100 at a constant or variable rate. The pump 130 may be used if the flow from the gas stream's back pressure is insufficient or inconsistent. The system 100 is preferably free from leaks. If the sample gas is volatile or flammable in nature, the system 100 is preferably contained in an explosion proof or purged enclosure.

The sample gas flows through the sample inlet line 112 into the valve 122. As illustrated, the valve 122 is a three-way valve that outlets either to the zero-filter 114 or to the first plain line 124a. If the valve 122 is open to the zero-filter 114, all of the chlorides are removed from the sample gas stream. If the valve 122 is open to the first plain line 124a, then the sample gas simply flows unaltered through the first plain line 124a to the next component (e.g., RCl converter 116).

After the sample gas flows through either the zero-filer 114 or the first plain line 124a, the sample gas flow is directed to the RCl converter 116 via the connector 126. The RCl converter 116 transforms RCl to HCl in the manner described above with respect to the RCl converter 16.

After the sample gas flows through the RCl converter 116, the sample gas is directed to the HCl analyzer 118 via the second plain line 124b. The HCl analyzer 118 is configured to detect and measure the HCl content in the sample gas, such as in the same manner described above with respect to the HCl analyzer 16.

In a first system mode, the valve 122 directs the sample gas to the zero-filter 114 and the analyzer reads or should be adjusted to read zero (i.e., no chlorine compounds detected). In a second system mode, the valve 122 directs the sample gas to the first plain line 124a, the sample gas flows through the RCl converter 116, and the HCl analyzer 118 detects and measures the total chloride amount (i.e., both the native HCl and the RCl that was converted to HCl). The system 100 may be operated in any of the first or second system modes.

After the sample gas flows through the HCl analyzer 118, the sample gas exits the system 100 through the exhaust line 120. The sample gas may be exhausted wherever the operator or system designer deems it appropriate to do so.

Similar to system 10 (FIG. 1), the system 100 may include an HCl scrubbing after the HCl analyzer 118 or after the exhaust line 120 to prevent damage to equipment and ensure operator safety. Also similarly to system 10, the system 100 may include a system controller that is operably coupled to at least the valve 122, the RCl converter 116, the HCl analyzer 118, and/or the pump 130 to control the operation thereof and/or to control the one or more operational modes of the system 100.

As used herein, an "operable connection," or a connection by which entities are "operably connected," is one in which signals, physical communications, or logical communications may be sent or received. Typically, an operable connection includes a physical interface, an electrical interface, or a data interface, but it is to be noted that an operable connection may include differing combinations of these or other types of connections sufficient to allow operable control. For example, two entities can be operably connected by being able to communicate signals to each other directly or through one or more intermediate entities like a processor, operating system, a logic, software, or other entity. Logical or physical communication channels can be used to create an operable connection.

It is understood that embodiments of the subject matter described in this disclosure can be implemented in combination with digital electronic circuitry, controllers, processors, computer software, firmware, and/or hardware. For example, embodiments may be implemented in a measurement system that uses one or more modules of computer program with instructions encoded on a non-transitory computer-readable medium for execution by, or to control the operation of, data processing apparatus. The operations may include physical manipulations of physical quantities. Usually, though not necessarily, the physical quantities take the form of electrical or magnetic signals capable of being stored, transferred, combined, compared, and otherwise manipulated in a logic and the like.

It will be appreciated that the processes may be implemented using various programming approaches like machine language, procedural, object oriented or artificial intelligence techniques. In one example, methodologies are implemented as processor executable instructions or operations provided on a computer-readable medium. Thus, in one example, a computer-readable medium may store processor executable instructions operable to perform a method. The computer-readable medium may be a hard-drive, a machine-readable storage device, a memory device, or a combination of one or more of the foregoing. The controller may include all apparatus, devices, and machines for processing data, including by way of example a programmable processor, a computer, or multiple processors or computers.

The controller may include, in addition to hardware, code that creates an execution environment for the computer program in question. The computer program (also referred to as software or code), may be deployed in any form, including as a stand-alone program or as a module, component, subroutine, or other unit suitable for use in a computing environment. The computer program may be deployed to be executed on one computer or on multiple computers that are located at one site or distributed across multiple sites and interconnected by a communication network. The processor may include all apparatus, devices, and machines suitable for the execution of a computer program, which may include, by way of example, both general and special purpose microprocessors, and any one or more processors of any kind of digital computer. Generally, the processor will receive instructions and data from a read-only memory or a random-access memory or both. The computer may include, or be operatively coupled to receive data from or transfer data to, or both, one or more mass storage devices for storing data. Devices suitable for storing computer program instructions and data include all forms of non-volatile memory, media and memory devices, including by way of example semiconductor memory devices. The processor and the memory can be supplemented by, or incorporated in, special purpose logic circuitry.

To provide for interaction with a user, embodiments may be implemented using a computer having a display device and an input device. Embodiments may include a computing system that includes a back-end component (e.g., as a data server), or that includes a middleware component (e.g., an application server), or that includes a front-end component (e.g., a client computer having a graphical user interface through which a user can interact with an implementation of the subject matter described is this specification), or any combination of one or more such back-end, middleware, or front-end components. The components of the system can be interconnected by any form or medium of digital data communication.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A measurement system for real-time measurement of RCI content in a sample gas taken from a combustion or process gas stream, the system comprising:
   a sample inlet for receiving the sample gas from the combustion or process gas stream;
   an RCI converter downstream of the sample inlet for receiving the sample gas, the RCI converter being configured to convert RCI contained in the sample gas to HCl; and
   an HCl analyzer downstream of the RCI converter, the RCI converter being configured to measure an amount of HCl contained in the sample gas;
   wherein the system is configured to operate in at least a first state, in which the sample gas flows through the RCI converter and the RCI contained in the sample gas is converted to HCl thereby forming a converted sample gas, said converted sample gas flowing downstream to the HCl analyzer when the system is in the first state for measuring the amount of HCl contained therein;
   wherein the system is configured to operate in at least a second state, in which at least some of the sample gas bypasses the RCI converter and avoids conversion of the RCI to HCl as unconverted sample gas, said unconverted sample gas flowing into the HCl analyzer for measuring the amount of HCl contained therein; and
   wherein the RCI content in the sample gas is determinable based upon a difference in at least: (i) the amount of HCl contained in the converted sample gas as measured by the HCl analyzer when the system is in the first state, and (ii) the amount of HCl contained in the unconverted sample gas as measured by the HCl analyzer when the system is in the second state.

2. The system according to claim 1, further comprising:
a valve interposed between the sample inlet and the HCl analyzer in a gas circuit of the system;
wherein the valve is configured to operate in a first state corresponding to the first state of the system in which the valve is configured to open a flow path of the gas circuit that directs the sample gas to flow through the RCI converter to the HCl analyzer as the converted sample gas; and
wherein the valve is configured to operate in a second state corresponding to the second state of the system in which the valve is configured to close the flow path of the gas circuit to prevent the sample gas from flowing from the RCI converter to the HCl analyzer, the gas circuit being configured to direct the at least some of the sample gas to bypass the RCI converter and flow into the HCl analyzer as unconverted sample gas when the valve is in the second state.

3. The system according to claim 2, wherein the valve is disposed in the gas circuit upstream of the RCI converter.

4. The system according to claim 2, wherein the valve is a diverter valve that is configured to direct the sample gas to the RCI converter when in the first state, or is configured to divert the sample gas to bypass the RCI converter when in the second state.

5. The system according to claim 1, further comprising a zero-filter downstream of the sample inlet and upstream of the HCl analyzer, the zero-filter being configured to filter both HCl and RCI out of the sample gas.

6. The system according to claim 5, further comprising a second valve upstream of the zero-filter, the second valve being configured to divert the sample gas to either the zero-filter or a first plain line fluidly connected to the RCI converter and the HCl analyzer.

7. The system according to claim 1, further comprising a pump that is configured to convey the sample gas through the system.

8. The system according to claim 7, wherein the pump is located downstream of the HCl analyzer and upstream of an exhaust of the system.

9. The system according to claim 1, wherein the HCl analyzer is configured to determine the RCI content in the sample gas based upon the difference in at least: (i) the amount of HCl contained in the converted sample gas measured by the HCl analyzer, and (ii) the amount of HCl contained in the unconverted sample gas measured by the HCl analyzer.

10. The system according to claim 1, further comprising a controller operably connected to the RCI converter and configured to control one or more parameters associated with the conversion of the RCI contained in the sample gas to HCl.

11. The system according to claim 10, wherein the controller is configured to control a temperature of the RCI converter in a range of 50° C. to 500° C.

12. The system according to claim 2, further comprising a controller operably connected to the valve and configured to switch the valve between the first and second states of the valve.

13. The system according to claim 8, further including a controller operably connected to the pump and configured to control a flow rate of the sample gas through the system.

14. A refinery having the combustion or process gas stream in combination with the measurement system according to claim 1.

15. A system for real-time measurement of total chloride content of HCl and RCI in a combustion or process gas, the system comprising:
an inlet for receiving the combustion or process gas;
an RCI converter downstream of the inlet and configured to convert RCI contained in the combustion gas to HCl; and
an HCl analyzer downstream of the RCI converter, the HCL analyzer being configured to measure an amount of HCl in the combustion or process gas;
wherein the HCl analyzer is configured to determine the total chloride content of HCl and RCI in the combustion or process gas based upon the measured amount of HCl in the process gas received from the RCI converter, and is configured to output the results.

16. The system according to claim 15, further comprising a zero-filter upstream of the HCl analyzer, and a valve upstream of the zero-filter, the valve being configured to divert the combustion or process gas to either the zero-filter or a first plain line.

17. A method of real time speciated measurement RCI in a combustion or process gas, the method comprising:
providing the system according to claim 1;
setting an operation mode of the system to a first system mode, the first system mode including bypassing the RCI converter such that the HCl analyzer measures the amount of HCl in the unconverted sample gas;
setting an operation mode of the system to a second system mode, the second system mode including directing the sample gas to the RCI converter to convert the RCI to HCl thereby forming the converted sample gas, such that the HCl analyzer measures the amount of HCl in the converted sample gas; and
calculating a difference between the measurement from the first mode and the measurement from the second mode to determine the RCI concentration in the sample gas.

18. A method of real time total measurement of HCl and RCI in a combustion or process gas, the method comprising:
providing the system according to claim 15;
setting an operation mode of the system to a first system mode, the first system mode including bypassing a zero-filter and directing the sample gas to flow through the RCI converter such that the HCl analyzer measures the amount of HCl in the sample gas.

19. A method of real-time measurement of RCI content in a sample gas taken from a combustion or process gas stream, the method comprising:
(i) conveying the sample gas from the combustion or process gas stream into an inlet of a measurement system;
(ii) operating the measurement system in a first mode, including:
conveying the sample gas from the inlet to an RCI converter;
converting the RCI contained in the sample gas to HCl with the RCI converter, thereby forming a converted sample gas;
conveying the converted sample gas to an HCl analyzer;
measuring an amount of HCl in the converted sample gas with the HCl analyzer;
(iii) operating the measurement system in a second mode, including:
conveying the sample gas from the inlet;
bypassing the RCI converter such that the sample gas is unconverted sample gas;

conveying the unconverted sample gas to the HCl analyzer;

measuring an amount of HCl in the unconverted sample gas with the HCl analyzer; and (iv) determining an amount of RCl in the sample gas by calculating a difference between the measurement from the first mode and the measurement from the second mode.

\* \* \* \* \*